United States Patent [19]

Puttock et al.

[11] 4,263,442
[45] Apr. 21, 1981

[54] PROCESS FOR THE PREPARATION OF 2,3-DIHYDRO-5,6-DIPHENYL-1,4-OXATHIIN

[75] Inventors: Michael A. Puttock, Guelph; Ethel E. Felauer, Arkell; Bruce A. Graham, Guelph, all of Canada

[73] Assignee: Uniroyal Ltd., Ontario, Canada

[21] Appl. No.: 157,725

[22] Filed: Jun. 9, 1980

[30] Foreign Application Priority Data

May 2, 1980 [CA] Canada ................................. 351139

[51] Int. Cl.³ ......................................... C07D 327/06
[52] U.S. Cl. ..................................................... 549/14
[58] Field of Search ......................................... 549/14

[56] References Cited

PUBLICATIONS

Marshall et al., J. Chem. Soc., 1959, pp. 2360 to 2363.
Marshall et al., Chem. Abstracts, vol. 54, cols. 2341-2342, (1960).

*Primary Examiner*—John D. Randolph
*Attorney, Agent, or Firm*—James J. Long

[57] ABSTRACT

2,3-Dihydro-5,6-diphenyl-1,4-oxathiin is prepared by reacting benzoin and 2-mercaptoethanol in an alkanol solvent of 2 to 8 carbon atoms and an acidic catalyst. The use of alcohol solvent in lieu of aromatic solvents gives much greater purity with much better yields.

7 Claims, No Drawings

PROCESS FOR THE PREPARATION OF 2,3-DIHYDRO-5,6-DIPHENYL-1,4-OXATHIIN

This invention relates to a method of making 2,3-dihydro-5,6-diphenyl-1,4-oxathiin.

Oxathiin compound I (2,3-dihydro-5,6-diphenyl-1,4-oxathiin) is useful as a herbicide and a plant growth regulant as taught by Graham, et al. in U.S. Pat. Nos. 3,947,264, Mar. 30, 1976; 4,020,168, Apr. 26, 1977; 4,043,792, Aug. 23, 1977; and 4,127,402, Nov. 28, 1978.

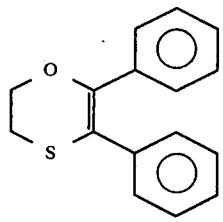

The conventional process for the manufacture of 1,4-oxathiins entails the reaction of an alpha-haloketone with 2-mercaptoethanol in the presence of a base and subsequent cyclization in the presence of an acid catalyst. Thus, compound I may be prepared by the reaction of desyl chloride and 2-mercaptoethanol in toluene solvent in the presence of ammonia, washing with water to remove the ammonium chloride by-product and then cyclizing in the presence of para-toluenesulfonic acid. A further wash with aqueous caustic is then required to remove impurities so that a pure product can be isolated. Furthermore, desyl chloride must be prepared from deoxybenzoin or benzoin by chemical processes that typically produce equimolar quantities of hydrogen chloride and sulfur dioxide gases. These gases, as well as the aqueous washes already mentioned, must be especially treated or be discharged as environmental pollutants. This process is, therefore, rather costly because of the number of steps involved, and because of the number of environmentally damaging by-products which require special treatment or disposal.

A second method of preparing compound I was reported by Marshall and Stevenson [J. Chem. Soc. 2360-3 (1959)]. This process involves the direct reaction of benzoin with 2-mercaptoethanol in toluene solvent. The method, as presented, has several serious shortcomings which make it impractical. The reported yield is low; unreacted benzoin contaminates the product at the end of the reaction; a large amount of the 2-mercaptoethanol is converted to an insoluble polymer which contaminates the product; an aqueous caustic wash is required to purify the crude product; and the isolation of the desired I is tedious and commercially impractical. This process would be even more expensive than the conventional process because of these shortcomings. It also presents a new problem, namely the disposal of large quantities of the insoluble polymer of 2-mercaptoethanol.

It is, therefore, an object of this invention to provide an economical, one-step process for the preparation of I by the direct reaction of benzoin and 2-mercaptoethanol in the presence of an aliphatic alcohol having from 2 to 8 carbon atoms and an acid catalyst.

It is a further object of this invention to provide a relatively pollution-free process for the preparation of I.

It has been shown that, contrary to Marshall and Stevenson's statement that benzoin and 2-mercaptoethanol "did not react in boiling benzene", the reaction at 80° (temperatures are expressed herein on the Celsius scale) using benzene (or toluene under vacuum) as solvent gives a considerable improvement in yield. However, a 40% excess of 2-mercaptoethanol is required for a yield of 70–75%. Thus, a large amount of polysulfide polymer as well as the 25–30% of unreacted benzoin contaminates the product I and purification is difficult.

We have shown that polymer formation is decreased when the reaction is carried out in certain solvents with only a 20% excess of 2-mercaptoethanol. One such solvent is cyclohexane. It is advantageous in that the polysulfide polymer is only very slightly soluble in cyclohexane. Thus, the clear solution of benzoin and I can be decanted. Although yields of I are of the order of 70%, the problem remains that it is extremely difficult to separate I from the 30% of unreacted benzoin.

Another of these solvents is 1,2-dichloroethane. It has the advantage of suppressing the formation of polymeric 2-mercaptoethanol almost entirely. Unfortunately, as the yield of I does not increase significantly above 70%, its purification is not simplified in comparison with the products of previous methods.

In accordance with this invention, it has now been found, unexpectedly, that there is a remarkable improvement in the process when benzoin and 2-mercaptoethanol react in the presence of an aliphatic alcohol (alkanol) containing 2 to 8 carbon atoms and an acidic catalyst. The process, in which benzoin reacts with 2-mercaptoethanol in the liquid phase, is carried out at a temperature of about 80° to 200° in the presence of an acidic catayst and an alcohol, selected from the group of primary and secondary aliphatic alcohols containing 2 to 8 carbon atoms. The water produced in the reaction is removed. An inert solvent may be present to facilitate this water removal. The preferred temperature range is 100° to 125°. The product 2,3-dihydro-5,6-diphenyl-1,4-oxathiin (I) may be easily recovered from the reaction mixture by distillation of the solvent from the crude product, followed by crystallization of the product from a solvent, such as isopropyl alcohol. It can be seen that, except for a small amount of viscous by-product left in the recrystallizing solvent, the process is pollution free in that no unnecessary steps are involved, no noxious gases are evolved, nor is further treatment with aqueous washes required.

The process of the invention described herein folows the reaction sequence.

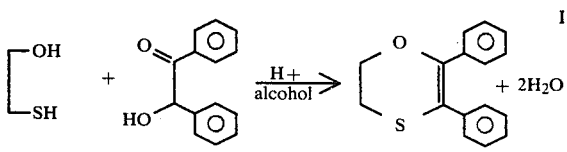

The two reactants, 2-mercaptoethanol and benzoin, are soluble in aliphatic alcohols containing 2 to 8 carbon atoms at temperatures above about 50°–60°. This solubility is not changed by the addition of an inert solvent, such as benzene or toluene, that may be added to facilitate water removal. It is preferred that the mole ratio of 2-mercaptoethanol to benzoin be in the range of about 1:1 to about 1.2:1 although higher or lower ratios can be used with little advantage.

When the alcohol is used alone, as solvent for the reaction, a weight ratio of alcohol to benzoin about 0.5:1 to about 10:1, preferably about 2:1 to about 3:1, is used, for ease of handling. In the presence of an inert solvent, a weight ratio of alcohol to benzoin about 0.01:1 to about 9:1, preferably about 0.15:1 to about 0.3:1, is used, while the overall ratio of solvent to reactants of about 0.5:1 to about 10:1, preferably about 2:1 to about 3:1, is maintained. The lower molecular weight alcohols work best with relatively higher mole % (vs benzoin) of alcohol.

Various aliphatic alcohols containing from 2 to 8 carbon atoms can be used as solvent for the reaction. Representative of these alcohols are ethanol, propanol, butanol, 1-methylpropanol, 1,3-dimethylbutanol, octanol and isooctanol. Propanol and butanol are preferred.

The presence of an inert solvent is not critical although it can serve to facilitate the removal of water formed during the reaction. One convenient method of removing water comprises adding to the reaction mixture a quantity of volatile, water-immiscible, inert azeotroping agent for water, performing the preparation at reflux, collecting the condensed reaction vapors and allowing them to separate into an aqueous phase and an azeotropic agent phase (e.g., in a Dean-Stark trap), and then returning only the latter to the reaction mixture. Suitable inert solvents for this purpose are benzene and toluene, or the alcohol may serve this purpose (e.g., butanol). Water removal from the reaction mixture may also be effected by other methods such as by contacting the condensed reaction vapors with an inert drying agent (e.g., granular anhydrous magnesium sulfate) before returning them to the reaction mixture.

The catalyst is present in the reaction mixture in an amount of from about 0.0001 to about 0.1 g per g of benzoin (reacted). The preferred catalyst level is an amount of from about 0.005 to about 0.02 g per g of benzoin. The preferred catalysts are the aryl sulfonic acids (e.g., p-toluenesulfonic, 4-bromobenzenesulfonic, benzenesulfonic and napththalenesulfonic acids) with toluenesulfonic acid being most preferred.

This reaction may be operated as either a batch or semicontinuous process. When the former procedure is employed, the full quantities of benzoin, 2-mercaptoethanol and catalyst are charged to the reactor initially. When the latter procedure is employed, the full quantities of benzoin and catalyst, but only a portion of the 2-mercaptoethanol, are charged to the reactor initially and the reaction mixture refluxed while the remainder of the 2-mercaptoethanol is added gradually over the course of the reaction. In both processes, water is removed. The preferred method of removing water is the azeotropic distillation described above.

Commercial grades of the starting materials, benzoin and 2-mercaptoethanol, are acceptable.

The product 2,3-dihydro-5,6-diphenyl-1,4-oxathiin (I) may be recovered from the liquid phase reaction mixture by conventional methods, such as crystallization from the reaction mixture upon cooling or by removal of the solvent under vacuum and crystallization of the crude product from a solvent such as isopropanol. (Both methods are described in the examples herein). The residues from either process may be charged to the next batch to further enhance the recovery of product and reduce the wastes as described in the Examples.

Several important advantages are offered by the process of the invention. It involves only one chemical step which may be performed under a single set of reaction conditions. The cost of reactants other than benzoin and 2-mercaptoethanol, e.g., sulfuryl chloride, is eliminated. Benzoin is considerably more available and less expensive than deoxybenzoin, the starting material in U.S. Pat. No. 4,020,168. The reaction products are the desired 1,4-oxathiin and water. No equimolar quantities of reaction products such as sulfur dioxide and hydrogen chloride, which must be treated in order to avoid damage to the environment, are generated. No aqueous washes, which must be separately treated so as not to cause pollution, are required to remove inorganic or organic impurities (such that the reaction sequence may proceed or the recovery) of the product is enhanced). No difficult to remove starting material contaminates the desired product and no difficult to handle polymers of 2-mercaptoethanol are produced as in the process of Marshall and Stevenson.

The process is practical and very well suited for commercial scale production. Other advantages are revealed in this application.

The alkanol is believed to be more than merely an inert solvent although it can play that role as well. The benzoin that is not converted to the desired product is apparently present as another compound believed to be the benzoin alcohol ether. The alkanol is also thought to react with 2-mercaptoethanol, preventing the formation of 2-mercaptoethanol polymer.

The following examples serve to illustrate specific embodiments of this invention.

EXAMPLE 1

Benzoin (106 g, 0.5 mole), 2-mercaptoethanol (43 g, 0.55 mole), and p-toluenesulfonic acid (pTSA) (5 g) are charged into a 2-liter 3-neck flask. n-Butanol (1200 mL) is added and the mixture stirred with a mechanical stirrer. The reaction is heated to reflux and the distillate passed through a vacuum-jacketed column (18 in by ¾ in) packed with porcelain saddles. A Dean-Stark trap is placed at the top of the column to assist in the separation of the aqueous layer from the butanol/water azeotrope. After water ceases to separate, distillate is slowly removed until the vapor temperature at the top of the column reaches 117°–118°, the boiling point of dry n-butanol. The reaction mixture is cooled and seeded, and the crystalline product separated by filtration. The filtrate is returned to the reactor along with further amounts of benzoin, 2-mercaptoethanol, and pTSA as specified above. Sufficient n-butanol is added to make up for that removed in the prior reaction. When the procedure is repeated five times, the overall isolated yield of 2,3-dihydro-5,6-diphenyl-1,4-oxathiin is 76% of theoretical.

|         | GRAMS YIELD | % YIELD | M.P.(°) | HOURS REACTION TIME |
|---------|-------------|---------|---------|---------------------|
| Run 1   | 39          | 30.7    | 61–2    | 9                   |
| Run 2   | 129         | 101.6   | 62–3    | 9.5                 |
| Run 3   | 106         | 83.5    | 62–3    | 8                   |
| Run 4   | 79          | 62.2    | 62–3    | 7.5                 |
| Run 5   | 119         | 93.7    | 60–2    | 5.5                 |
| Run 6   | 108         | 85.0    | 61–2    | 4                   |
| Overall | 580         | 76      |         |                     |

EXAMPLE 2

Benzoin (106 g, 0.5 mole), 2-mercaptoethanol (43 g, 0.55 mole), and pTSA (5 g) are charged into a 2-liter 3-neck flask. A mixture of butanol+cylclohexane (1000 mL+200 mL) is added and the mixture stirred with a mechanical stirrer. The reaction is heated to reflux and the distillate passed through a vacuum-jacketed column (18 in by ¾ in) packed with porcelain saddles. A Dean-Stark trap is placed at the top of the column to assist in the separation of the aqueous layer from the azeotrope. After water ceases to separate (about 6.5 hr), the solvent is removed under vacuum. The dark yellow oil remaining is dissolved in hot isopropanol (about 700 mL) and cooled with stirring and seeded). The almost white crystalline product is separated by filtration and dried. Yield 89 g, 70%.

EXAMPLE 3

The procedure of Example 2 was followed except that propanol+benzene (1000 mL to 200 mL) was used as the solvent. After about 7.5 hours of reflux, the yield of I was 76 g, 60%.

The isopropanol from the crystallization was evaporated under vacuum and the oily residue added to a further reaction otherwise identical to the above. After about 6 hours of reflux, the yield of I was 114 g, 90%.

The average yield of the two was 75%.

EXAMPLE 4

The procedure of Example 2 was used except that butanol+toluene (400 mL+200 mL) was used as the solvent. After about 7 hours of reflux, the yiedld of I was 93 g, 73%.

EXAMPLE 5

The procedure of Example 3 was used except that butanol+toluene (100 mL+400 mL) was used as the solvent. The yields after 7 hours and 5 hours of reflux were respectively 82% and 89% for an average of 85.5%.

EXAMPLE 6

The procedure of Example 2 was used except that octanol+toluene (10 mL+490 mL) was used as the solvent. After about 6 hours of reflux the yield was 90 g, 71%.

EXAMPLE 7

Benzoin (106 g, 0.5 mole), 2-mercaptoethanol (41 g, 0.525 mole) and pTSA (1 g) were refluxed in a mixture of butanol (25 mL) and toluene (225 mL) using the procedure of Example 2. After 5.5 hours the yield of I was 100 g, 79%. Analysis of the product by High Pressure Liquid Chromatography (HPLC) showed it to be about 99% pure.

EXAMPLE 8

The procedure of Example 7 was used except that 47 g of 2-mercaptoethanol were added in portions. After about 11 hours of reflux the yield of I was 101 g, 80%. Analysis of the residue by HPLC showed that it contained a further 20 g of I for an overall conversion of benzoin to I of 95%.

EXAMPLE 9

Benzoin (21.2 g, 0.1 mole), 2-mercaptoethanol (9 mL, 0.12 mole) and pTSA (1 g) were refluxed in butanol (200 mL) solvent. The vapors were condensed, passed through a bed of anhydrous magnesium sulfate in a Soxhlet, and returned to the reaction mixture. After about 16 hours, the reaction mix was cooled to about 0° and product I filtered and dried. Yield 16 g. Butanol was added to the filtrate until a volume of 200 mL was present and, together with further quantities of reactants and catalyst as above, the filtrate was returned to the reactor. After a further 16 hours reaction, the second crop of I weighed 19.5 g. The average yield over the two runs was 70%.

What is claimed is:

1. A method of making 2,3-dihydro-5,6-diphenyl-1,4-oxathiin comprising bringing together benzoin and 2-mercaptoethanol in the presence of an alkanol containing 2 to 8 carbon atoms and an acidic catalyst, removing water of reaction, and thereafter recovering 2,3-dihydro-5,6-diphenyl-1,4-oxathiin.

2. A method as in claim 1 in which the reaction temperature is from 80° C. to 200° C. and the mole ratio of 2-mercaptoethanol to benzoin is in the range of 1:1 to 1.2:1.

3. A method as in claim 1 in which the reaction mixture further contains an inert solvent for the entrainment and removal of water of reaction.

4. A method as in claim 1 in which the weight ratio of alkanol to benzoin is 0.5:1 to 10:1.

5. A method as in claim 3 in which the weight ratio of alkanol to benzoin is 0.01:1 to 9:1 and the overall ratio of solvent to reactants is 0.5:1 to 10:1.

6. A method as in claim 1 in which the acid catalyst is p-toluenesulfonic acid.

7. A method as in claim 1 in which the alkanol is propanol or butanol.

* * * * *